US012766018B2

(12) United States Patent
Sachar et al.

(10) Patent No.: US 12,766,018 B2
(45) **Date of Patent: *Oct. 20, 2026**

(54) TRANSLUMINAL ANGIOPLASTY DEVICES AND METHODS OF USE

(71) Applicant: Contego Medical, Inc., Raleigh, NC (US)

(72) Inventors: Ravish Sachar, Raleigh, NC (US); Eugene Serina, Raleigh, NC (US); Udayan Patel, San Jose, CA (US)

(73) Assignee: Contego Medical, Inc., Raleigh, NC (US)

( * ) Notice: Subject to any disclaimer, the term of this patent is extended or adjusted under 35 U.S.C. 154(b) by 29 days.

This patent is subject to a terminal disclaimer.

(21) Appl. No.: 18/903,648

(22) Filed: Oct. 1, 2024

(65) Prior Publication Data

US 2025/0099278 A1 Mar. 27, 2025

Related U.S. Application Data

(63) Continuation of application No. 17/885,522, filed on Aug. 10, 2022, now Pat. No. 12,138,187, which is a
(Continued)

(51) Int. Cl.
*A61F 2/958* (2013.01)
*A61F 2/01* (2006.01)
(Continued)

(52) U.S. Cl.
CPC .............. *A61F 2/958* (2013.01); *A61F 2/013* (2013.01); *A61F 2/852* (2013.01); *A61F 2/915* (2013.01);
(Continued)

(58) Field of Classification Search
CPC .......... A61F 2/011; A61F 2/013; A61F 2/852; A61F 2/915; A61F 2/9517; A61F 2/958;
(Continued)

(56) References Cited

U.S. PATENT DOCUMENTS

| | | | |
|---|---|---|---|
| 4,655,771 A | 4/1987 | Wallsten et al. |
| 5,843,027 A | 12/1998 | Stone et al. |

(Continued)

FOREIGN PATENT DOCUMENTS

| | | |
|---|---|---|
| CA | 102227194 Z | 10/2011 |
| CA | 102753119 A | 10/2012 |

(Continued)

OTHER PUBLICATIONS

International Search Report and Written Opinion issued in International Patent Application No. PCT/US2017/066067, mailed Mar. 5, 2018.

(Continued)

*Primary Examiner* — Mohamed G Gabr
(74) *Attorney, Agent, or Firm* — Meunier Carlin & Curfman LLC

(57) ABSTRACT

A percutaneous transluminal angioplasty device includes a catheter defining one or more lumens. A filter is coupled to the catheter adjacent a distal end of the catheter, and the filter is movable between an unexpanded and expanded configuration via a filter activation wire that extends through a lumen. An expandable balloon is coupled to the catheter proximally of the filter, and a stent is disposed over at least a portion of the balloon. To deploy the stent to a target site, the filter is first moved into its expanded position via the filter activation wire. Then, the stent is expanded, and the balloon is inflated to expand the stent further radially. The balloon is then deflated, the filter is contracted, and the catheter, balloon, and filter are removed from the body.

20 Claims, 16 Drawing Sheets

Related U.S. Application Data continuation of application No. 17/179,739, filed on Feb. 19, 2021, now Pat. No. 11,865,022, which is a continuation of application No. 15/977,267, filed on May 11, 2018, now Pat. No. 10,932,929, which is a continuation of application No. 15/336,242, filed on Oct. 27, 2016, now Pat. No. 9,968,472.

(60) Provisional application No. 62/246,839, filed on Oct. 27, 2015.

(51) Int. Cl.

| | |
|---|---|
| *A61F 2/852* | (2013.01) |
| *A61F 2/915* | (2013.01) |
| *A61F 2/95* | (2013.01) |
| *A61F 2/966* | (2013.01) |
| *A61M 25/00* | (2006.01) |
| *A61M 25/10* | (2013.01) |

(52) U.S. Cl.

CPC ............... *A61F 2/966* (2013.01); *A61F 2/011* (2020.05); *A61F 2002/91558* (2013.01); *A61F 2002/91575* (2013.01); *A61F 2/9517* (2020.05); *A61F 2220/0091* (2013.01); *A61F 2230/001* (2013.01); *A61F 2230/0067* (2013.01); *A61F 2230/008* (2013.01); *A61F 2250/0017* (2013.01); *A61F 2250/0039* (2013.01); *A61M 25/0026* (2013.01); *A61M 2025/0037* (2013.01); *A61M 25/104* (2013.01); *A61M 2025/1081* (2013.01)

(58) Field of Classification Search

CPC ............ A61F 2/966; A61F 2002/91558; A61F 2002/91575; A61F 2220/0091; A61F 2230/001; A61F 2230/0067; A61F 2230/008; A61F 2250/0017; A61F 2250/0039; A61M 2025/0037; A61M 2025/1081; A61M 25/0026; A61M 25/104

See application file for complete search history.

(56) References Cited

U.S. PATENT DOCUMENTS

| | | | | |
|---|---|---|---|---|
| 5,913,895 | A | 6/1999 | Burpee et al. | |
| 6,245,611 | B1 | 6/2001 | Hashimoto et al. | |
| 6,391,050 | B1 * | 5/2002 | Broome | A61F 2/95 623/1.11 |
| 6,511,503 | B1 | 1/2003 | Burkett et al. | |
| 6,569,193 | B1 | 5/2003 | Stalker et al. | |
| 6,669,723 | B2 | 12/2003 | Killion et al. | |
| 6,736,840 | B2 | 5/2004 | Fischell et al. | |
| 7,169,165 | B2 | 1/2007 | Belef et al. | |
| 8,758,424 | B2 | 6/2014 | Sachar et al. | |
| 9,149,376 | B2 | 10/2015 | Beach et al. | |
| 9,510,947 | B2 | 12/2016 | Straubinger et al. | |
| 9,566,178 | B2 | 2/2017 | Cartledge et al. | |
| 9,968,472 | B2 | 5/2018 | Sachar | |
| 12,076,259 | B2 * | 9/2024 | Sachar | A61F 2/915 |
| 12,138,187 | B2 * | 11/2024 | Sachar | A61F 2/966 |
| 2002/0016564 | A1 | 2/2002 | Courtney et al. | |
| 2002/0156523 | A1 | 10/2002 | Lau et al. | |
| 2003/0004535 | A1 | 1/2003 | Musbach et al. | |
| 2003/0055480 | A1 | 3/2003 | Fischell et al. | |
| 2003/0167084 | A1 | 9/2003 | Orlowski et al. | |
| 2004/0220607 | A1 | 11/2004 | Donovan et al. | |
| 2004/0230284 | A1 | 11/2004 | Headley et al. | |
| 2004/0236409 | A1 | 11/2004 | Duerig et al. | |
| 2005/0004594 | A1 | 1/2005 | Nool et al. | |
| 2005/0038466 | A1 | 2/2005 | O'Heeron et al. | |
| 2005/0038468 | A1 | 2/2005 | Panetta et al. | |
| 2005/0038503 | A1 | 2/2005 | Greenhalgh et al. | |
| 2005/0149166 | A1 | 7/2005 | Schaeffer et al. | |
| 2005/0228438 | A1 * | 10/2005 | Sachar | A61F 2/958 606/200 |
| 2007/0088430 | A1 | 4/2007 | Banas et al. | |
| 2007/0156168 | A1 | 7/2007 | Dunfee et al. | |
| 2007/0173929 | A1 | 7/2007 | Boucher et al. | |
| 2007/0185559 | A1 | 8/2007 | Shelso et al. | |
| 2008/0077223 | A1 | 3/2008 | Fischell et al. | |
| 2008/0228261 | A1 | 9/2008 | Anukhin et al. | |
| 2008/0269868 | A1 | 10/2008 | Bei et al. | |
| 2009/0105686 | A1 | 4/2009 | Snow et al. | |
| 2009/0192384 | A1 | 7/2009 | Fontius | |
| 2010/0036481 | A1 | 2/2010 | Dubrul et al. | |
| 2010/0268263 | A1 | 10/2010 | Edelman et al. | |
| 2011/0106238 | A1 | 5/2011 | Williamson | |
| 2012/0041469 | A1 | 2/2012 | Fischell et al. | |
| 2012/0277843 | A1 | 11/2012 | Weber et al. | |
| 2012/0330346 | A1 * | 12/2012 | Frimerman | A61F 2/958 606/200 |
| 2013/0261722 | A1 | 10/2013 | Hossainy | |
| 2014/0081371 | A1 | 3/2014 | Poehlmann et al. | |
| 2014/0142598 | A1 | 5/2014 | Fulton et al. | |
| 2014/0214067 | A1 | 7/2014 | Sachar et al. | |
| 2015/0005871 | A1 | 1/2015 | Shobayashi | |
| 2015/0051688 | A1 | 2/2015 | Cummins | |
| 2015/0133918 | A1 | 5/2015 | Sachar et al. | |
| 2015/0306361 | A1 | 10/2015 | Feig et al. | |
| 2016/0089228 | A1 | 3/2016 | Sachar et al. | |
| 2016/0213458 | A1 | 7/2016 | Sachar et al. | |

FOREIGN PATENT DOCUMENTS

| | | | |
|---|---|---|---|
| CN | 2532867 | Y | 1/2003 |
| CN | 1787793 | A | 6/2006 |
| CN | 2824874 | Y | 10/2006 |
| JP | H08509899 | A | 10/1996 |
| JP | 2004358242 | A | 12/2004 |
| JP | 2007512114 | A | 5/2007 |
| JP | 2007526020 | A | 9/2007 |
| JP | 2008301923 | A | 12/2008 |
| JP | 2009095682 | A | 5/2009 |
| JP | 2013154183 | A | 8/2013 |
| JP | 5586742 | B1 | 8/2014 |
| JP | 2014530689 | A | 11/2014 |
| JP | 2014530724 | A | 11/2014 |
| WO | 9526695 | A2 | 10/1995 |
| WO | 02/062266 | A2 | 8/2002 |
| WO | 2004/084764 | A2 | 10/2004 |
| WO | 2004/110304 | A2 | 12/2004 |
| WO | 2005053577 | A2 | 6/2005 |
| WO | 2010042458 | A1 | 4/2010 |
| WO | 2011/053693 | A1 | 5/2011 |
| WO | 2013/059776 | A1 | 4/2013 |
| WO | 2014085590 | A1 | 6/2014 |
| WO | 2017075273 | A1 | 5/2017 |

OTHER PUBLICATIONS

International Preliminary Report on Patentability issued by the International Bureau in International Application No. PCT/US2017/066067 on Jun. 27, 2019.

International Search Report and Written Opinion issued in International Patent Application No. PCT/US2016/059203, mailed Feb. 20, 2017.

International Preliminary Report on Patentability issued in International Patent Application No. PCT/US2016/059203, mailed May 11, 2018.

Communication Pursuant to Article94(3) issued for European Application No. 16791781.4, date Mar. 8, 2019, 5 pages.

Extended European Search Report, issued for Application No. 17880585.9, dated Jun. 22, 2020. 7 pages.

English Translation of Notice of Reasons for Rejection issued in JP2018- 522060, mailed Oct. 27, 2020.

Office Action issued for Chinese Application No. 201680069353.4, dated Jun. 19, 2019.

Office Action issued for Chinese Application No. 201680069353.4, dated Mar. 20, 2020.

(56) References Cited

OTHER PUBLICATIONS

Office Action issued in Chinese Application No. 202011071360.2 on May 6, 2021. 15 pages, including English translation.
Australian Intellectual Property Office. Examination Report No. 1 issued in Australian Application No. 2020260431 on Jun. 11, 2021. 4 pages.
Japanese Patent Office. Office Action issued in Japanese Application No. 2018-522060 on Aug. 2, 2021. 12 pages, including English translation.
English translation of Office Action for corresponding Japanese patent application No. 2022-076629, dated Apr. 10, 2023.

* cited by examiner

FIG. 13B
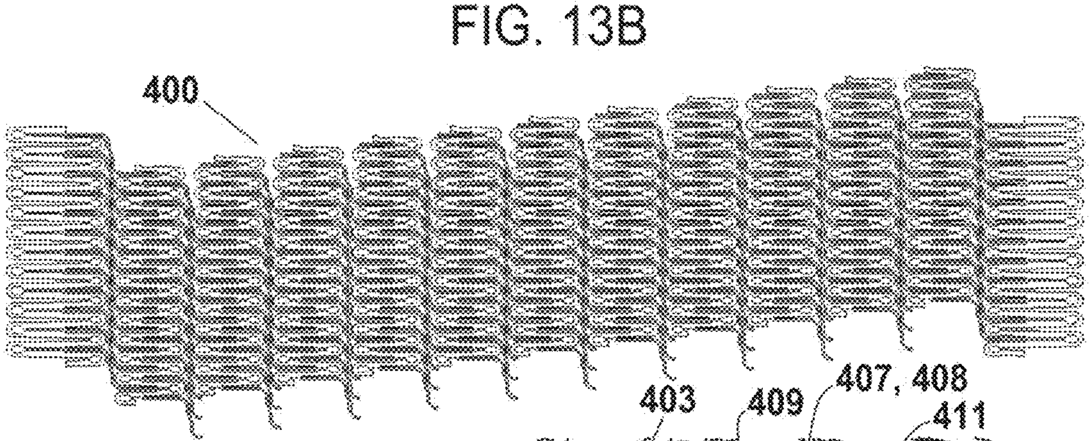
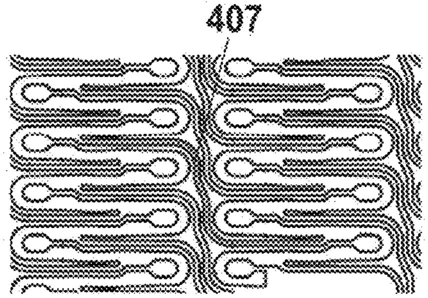
FIG. 13C
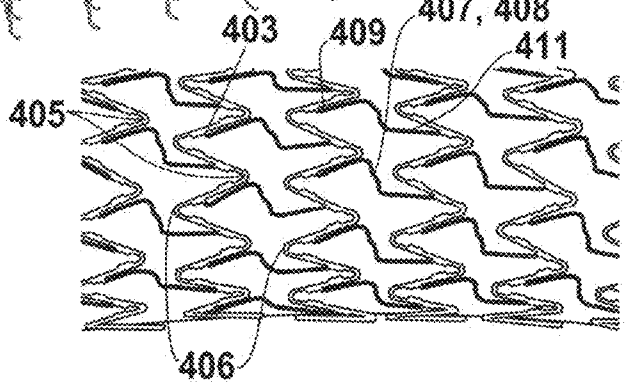
FIG. 13D

FIG. 14A
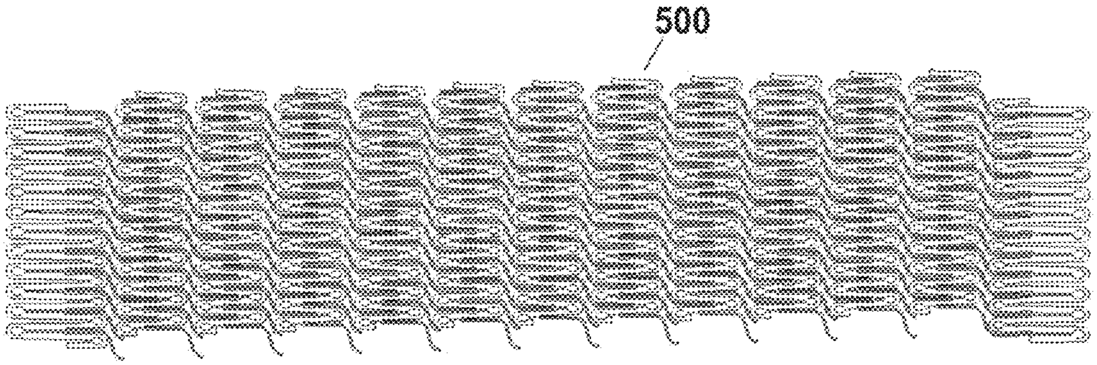
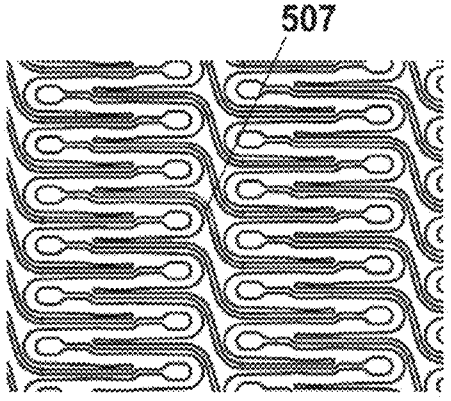
FIG. 14B
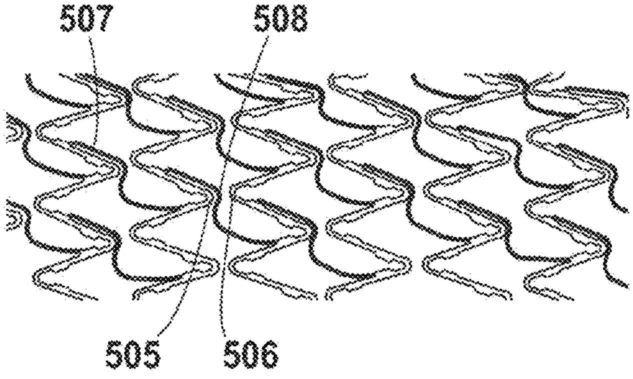
FIG. 14C

FIG. 15A
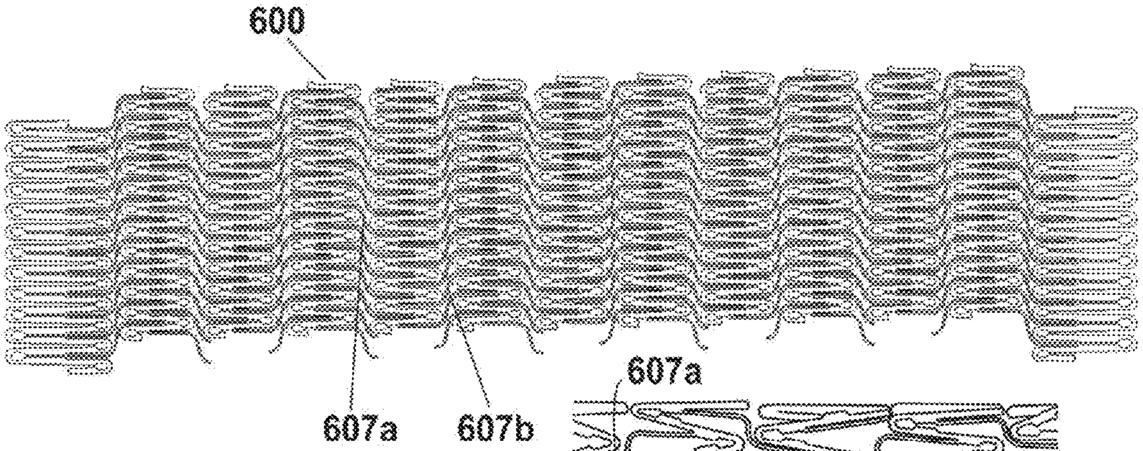
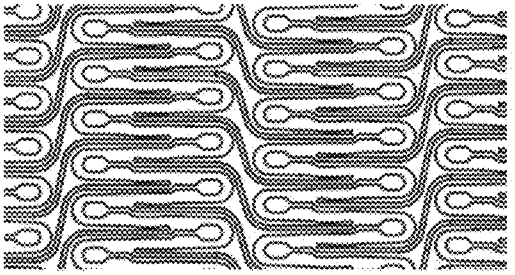
FIG. 15B
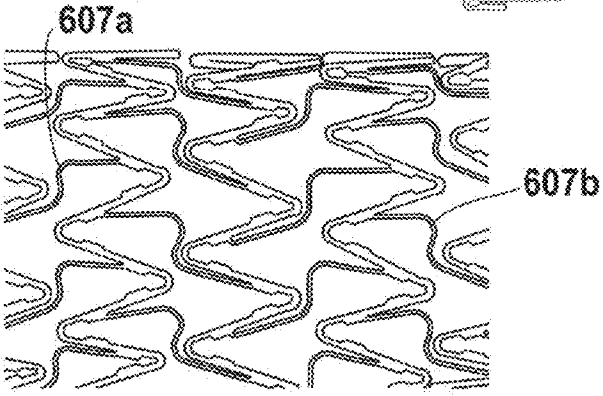
FIG. 15C

TRANSLUMINAL ANGIOPLASTY DEVICES AND METHODS OF USE

CROSS REFERENCE TO RELATED APPLICATION

This application is a continuation of U.S. application Ser. No. 17/885,522, filed Aug. 10, 2022, which is a continuation of U.S. application Ser. No. 17/179,739, filed Feb. 19, 2021 and issued as U.S. Pat. No. 11,865,022 on Jan. 9, 2024, which is a continuation of U.S. application Ser. No. 15/977,267, filed May 11, 2018 and issued as U.S. Pat. No. 10,932,929 on Mar. 2, 2021, which is a continuation of U.S. application Ser. No. 15/336,242, filed Oct. 27, 2016 and issued as U.S. Pat. No. 9,968,472 on May 15, 2018, which claims priority to U.S. Provisional Patent Application No. 62/246,839, entitled "Transluminal Angioplasty Device and Layered Stent," filed Oct. 27, 2015, the contents of which are herein incorporated by reference in their entirety.

BACKGROUND

Angioplasty catheters and stents are used in catheter-based procedures to open up a blocked vessel and restore blood flow. In general, physicians use separate devices to perform a single procedure. That is, when treating a vascular stenosis, separate devices/tools are used for embolic protection, stent deployment and post-dilation of the stent. The use of multiple devices to complete a single procedure has many drawbacks. For example, exchanging devices leads to longer procedure time, which poses patient safety risks; manipulation of multiple devices poses potential clinical risk; and interaction between multiple devices poses a risk of device failure. Thus, it is necessary for the surgeon to be trained on multiple devices, and there are higher costs to use multiple devices separately.

More specifically, when treating vascular lesions within the carotid arteries, there is a known risk of embolic material being liberated from the site of treatment during stent deployment or post-deployment balloon dilation of the stent. These embolic particles increase the risk of stroke. To address this risk, many types of vascular embolic filters have been designed. These filters are positioned within the artery past the lesion to be treated and remain in place during the entire procedure. To ensure adequate flow of blood during this time, the filter need to have large pores (100 microns or greater) and are thus only capable of capturing the biggest embolic particles. However, clinical research has shown that smaller diameter embolic particles can also cause stroke. Filter designed to capture small particles can only be left open for a short period. Thus, there is a need for a system that combines multiple products (embolic filter, stent and angioplasty balloon) into a single system that also allows for an embolic filter with small diameter pores (40 microns) to be used ensuring greater capture of embolic material.

In addition, stents are frequently used in conjunction with angioplasty devices in the treatment of vascular narrowing. Carotid stents, as well as stents used in other arterial and venous applications, need to provide sufficient radial strength to keep calcified lesions open and provide sufficient flexibility to travel through and conform to tortuous vessels. In addition, a low area between stent struts is needed to prevent plaque from embolizing through the stent and into the distal vasculature.

Accordingly, a need in the art exists for a treatment device that combines multiple tools needed to treat vascular stenosis into a single device.

SUMMARY

Various implementations include a percutaneous transluminal angioplasty device that includes a multi-lumen catheter, a filter, an expandable balloon, and a stent. The multi-lumen catheter has a proximal end and a distal end. The catheter defines a first lumen, a second lumen, and a third lumen, and each lumen extends through at least a portion of the catheter. The filter is disposed adjacent the distal end of the catheter, and the filter is movable between unexpanded and expanded configuration. The expandable balloon is disposed between the filter and the distal end of the catheter. The stent extends over at least a portion of the expandable balloon. In some implementations, the device also includes a movable sheath that extends over at least a portion of the stent, and a sheath wire is coupled to the movable sheath. The sheath wire extends through one of the lumens defined by the catheter, and movement of the sheath wire translates the sheath axially.

In some implementations, the stent is a self-expanding stent, and the self-expanding stent is constrained in place over at least a portion of the balloon by the movable sheath and expands in response to the movable sheath being moved axially away from the self-expanding stent. In some implementations, the sheath wire is moved axially to translate the sheath axially, and the axial movement of the sheath wire translates the sheath in the same direction as the axial movement of the sheath wire.

In some implementations, the device further includes a filter activation wire that is disposed within a first lumen, and a distal end of the filter activation wire is coupled to the filter.

In some implementations, the filter includes a filter frame and a filter membrane. The filter frame has a distal end and a proximal end, and the proximal end of the filter frame is fixedly coupled to the catheter. The distal end of the filter frame is slidably coupled to the catheter. The filter membrane has a distal end and proximal end, and the distal end of the filter membrane is fixedly coupled to the catheter distally of the proximal end of the filter membrane and the distal end of the filter frame. The proximal end of the filter membrane is fixedly coupled to a portion of the filter frame. The distal end of the filter activation wire is coupled to the distal end of the filter frame, and tensioning the filter activation wire in a proximal direction urges the distal end of the filter frame in axial proximal direction from an unexpanded configuration to an expanded configuration.

In some implementations, the device includes a handle coupled to a proximal end of the catheter, and the handle is coupled to the filter activation wire and the sheath wire. For example, in some implementations, the handle includes a first actuator coupled to the filter activation wire and a second actuator coupled to the sheath wire. The first actuator is manipulatable to expand and contract the filter via the filter activation wire, and the second actuator is manipulatable to axially move the sheath.

In some implementations, the third lumen is a balloon inflation lumen, and the catheter further defines an inflation port between an external surface of the catheter and the third lumen.

In some implementations, the catheter defines a guidewire port, and the guidewire port has a first opening defined by one of the first, second, or third lumen and a second opening defined by an exterior surface of the catheter. The first opening of the guidewire port is disposed distally relative to the second opening. In a further implementation, a guide wire is disposed within at least a portion of the first, second, or third lumen that defines the first opening of the guidewire port.

In some implementations, at least a portion of the filter has a radius in the expanded configuration that corresponds to an inner diameter of a blood vessel into which the filter is disposed.

In some implementations, the catheter includes a proximal portion and a distal portion, and the proximal portion is disposed adjacent a proximal end of the catheter and the distal portion is disposed adjacent a distal end of the catheter. The proximal portion of the catheter defines a sheath wire lumen, a proximal filter activation wire lumen, and a proximal balloon inflation lumen. The distal portion of the catheter defines a guidewire lumen, a distal filter activation wire lumen, and a distal balloon inflation lumen. In further implementations, the proximal balloon inflation lumen and the distal balloon inflation lumen are axially aligned, the proximal filter activation wire lumen and the distal filter activation wire lumen are axially aligned, and/or the sheath wire lumen and the guidewire lumen are axially aligned.

In some implementations, the stent includes a plurality of circumferentially arranged rings that are axially spaced apart, and the rings have a sinusoidal pattern around a circumference of each ring. Each ring is coupled to an axially adjacent ring by one or more axially elongated struts. For example, in certain implementations, the stent has a first end, a second end, a central portion, and a longitudinal axis extending between the first and second ends. A diameter of the central portion is less than a diameter of the first end and a diameter of the second end, and a diameter of the stent increases parabolically from the central portion toward each end.

In some implementations, the elongated struts are arranged in an s-pattern. The elongated struts in a first row have a first orientation, the elongated struts in a second row adjacent to the first row have a second orientation, and the first orientation and the second orientation are mirror images of each other.

In some implementations, each elongated strut is coupled between offset and opposing apexes of the sinusoidal pattern of adjacent ring segments such that the elongated strut extends around a portion of the circumference of the stent.

In some implementations, the stent comprises a first hollow tubular member and a second hollow tubular member, the first tubular member being coupled to the second tubular member such that a central portion of the first tubular member is disposed adjacent a central portion of the second tubular member. For example, in certain implementations, the first hollow tubular member includes a plurality of ring segments extending circumferentially around the first tubular member and an elongated strut connecting two adjacent ring segments located at a central portion of the first tubular member. The second hollow tubular member includes a second plurality of ring segments extending circumferentially round the second tubular member and a second elongated strut connecting two adjacent ring segments.

In some implementations, the stent includes first hollow tubular member and second hollow tubular member. The first tubular member is disposed adjacent an end portion of the second tubular member such that at least a portion of the first member overlaps a portion of the second member.

In some implementations, the stent is a self-expanding stent, a controlled/direct expansion stent, or a balloon expandable stent.

Various other implementations include a method of deploying a stent. The method includes: (1) routing a percutaneous transluminal angioplasty device through a body to a site of a vascular stenosis, the device includes a multi-lumen catheter, a filter, a stent, and an expandable balloon; (2) disposing a distal end of the catheter downstream of the vascular stenosis such that the stent is disposed radially inward of the vascular stenosis and the filter is disposed downstream of the vascular stenosis; (3) deploying the filter downstream of the vascular stenosis; (4) deploying the stent after the filter is deployed; (5) inflating the balloon to post-dilatate the stent; (6) deflating the balloon; (7) contracting the filter; and (8) removing the catheter from the body.

In some implementations, the device further includes an axially movable sheath, and the stent is disposed over at least a portion of the expandable balloon and at least a portion of the stent. And, the method further includes axially moving the sheath proximally to expose the stent and allow the stent to expand into an expanded position.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

Various implementations of a stent and a percutaneous transluminal angioplasty device are described in detail in the following drawings. The drawings are merely exemplary to illustrate the structure of stents/devices and certain features that may be used singularly or in combination with other features. The invention should not be limited to the examples shown.

FIGS. 13A-13D illustrate a stent according to another implementation;

FIGS. 14A-14C illustrate a stent according to another implementation;

FIGS. 15A-15C illustrate a stent according to another implementation;

DETAILED DESCRIPTION

Figure 1:
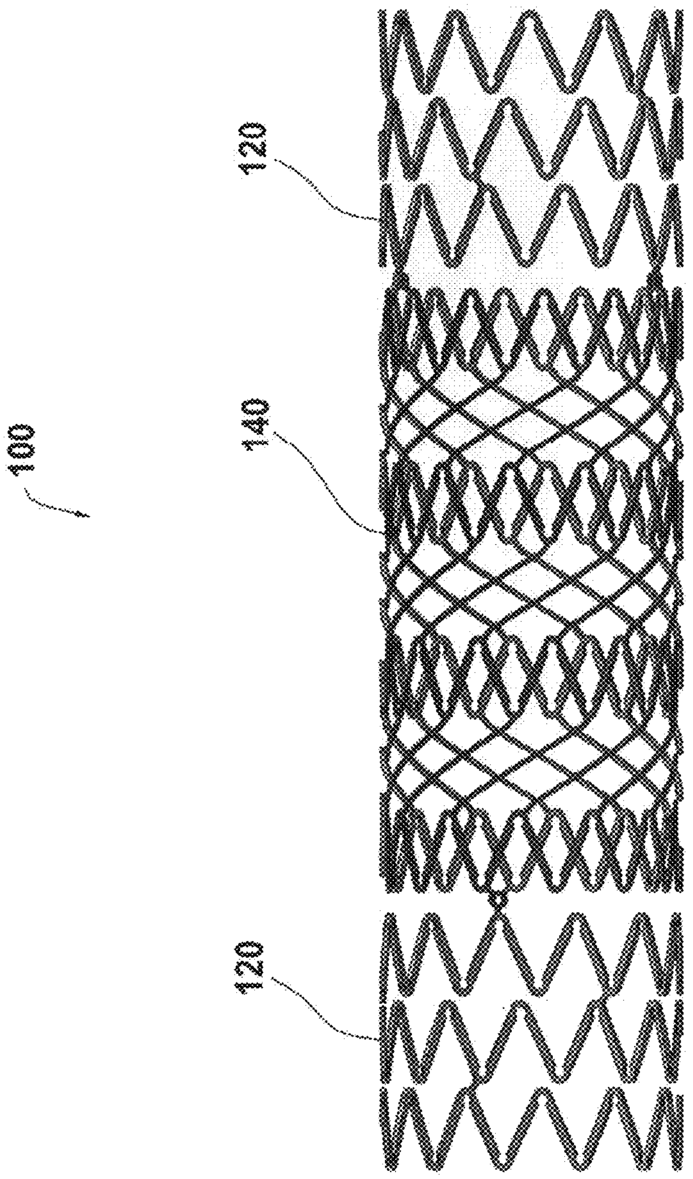
FIG. 1 is a side view of an exemplary layered stent according to one implementation.

Certain terminology is used in the following description for convenience only and is not limiting. The words “right,” “left,” “lower,” and “upper” designate direction in the drawings to which reference is made. The words “inner” and “outer” refer to directions toward and away from, respectively, the geometric center of the described feature or device. The words “distal” and “proximal” refer to directions taken in context of the item described and, with regard to the instruments herein described, are typically based on the perspective of the surgeon using such instruments. The terminology includes the above-listed words, derivatives thereof, and words of similar import.

Various implementations relate to percutaneous transluminal angioplasty devices and stents suitable for use therewith. FIG. 1 provides a side view of an exemplary layered stent 100 according to one implementation. The stent 100 includes first and second tubular members 120, 140. In one implementation, the first and/or second tubular members 120, 140 are self-expanding. In other implementations, the first and/or second tubular members 120, 140 are balloon-expandable. As will be described in more detail below, the first and second tubular members 120, 140 are coupled together such there is overlap of the two members 120, 140. For example, as illustrated in FIG. 1, the second tubular member 140 is coupled to the first tubular member 120 such that the central portion 122 of the first tubular member 120 is disposed adjacent the central portion 142 of the second tubular member 140. In other implementations (not shown), the second tubular member 140 extends over the first tubular member 120 at a location other than the central portion 122 of the first tubular member 120. For example, the second tubular member 140 may extend over a portion of the proximal or distal end 123, 125 of the first tubular member 120. Additionally, the second tubular member may have a length equal to the first tubular member and may extend over the entirety of the first tubular member 120.

Figure 2:
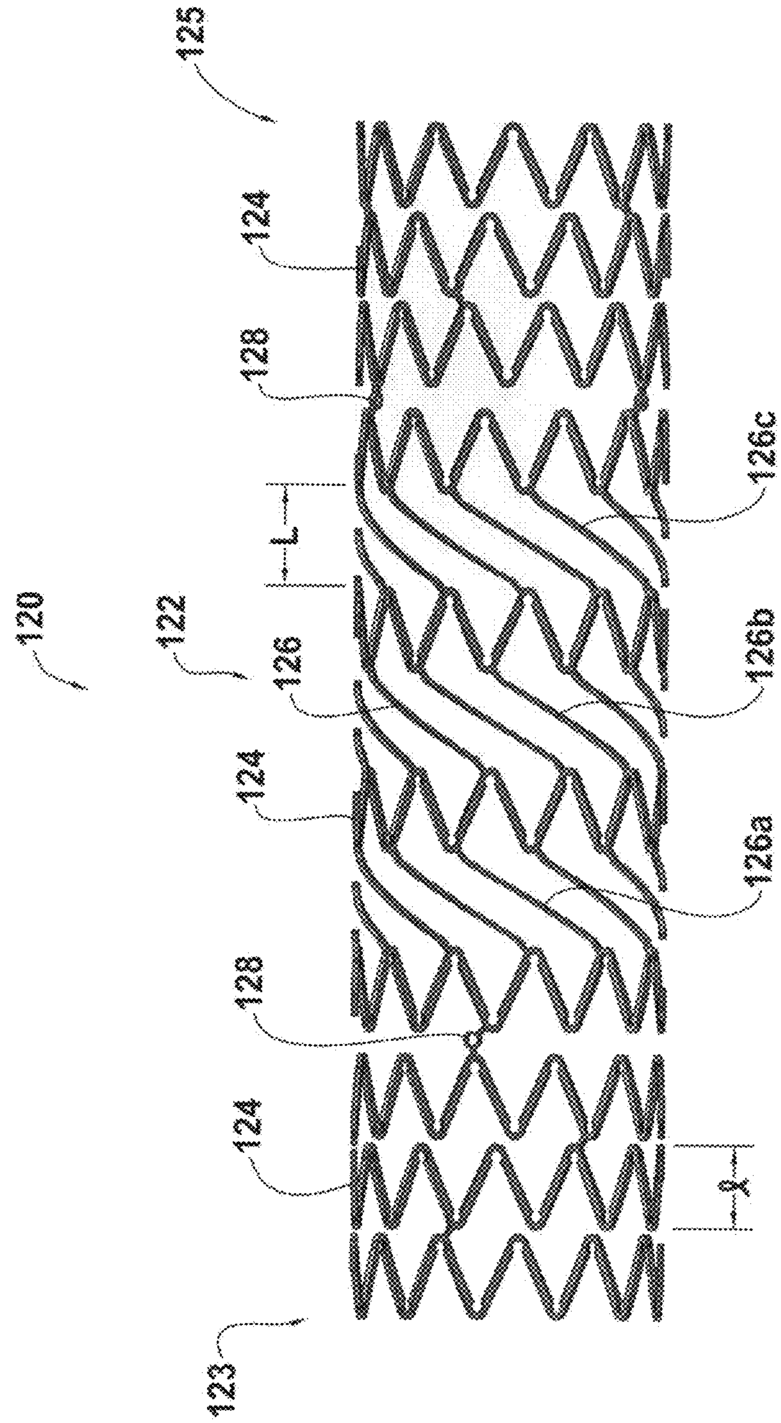
FIG. 2 is a side view of a first hollow tubular member of the stent in FIG. 1.

FIG. 2 provides a side view of an exemplary first hollow tubular member 120 according to one implementation. The first tubular member 120 includes a plurality of ring segments 124 extending circumferentially around the perimeter of the first tubular member 120. At least some of the ring segments 124 are connected by an elongated strut 126. As illustrated in FIG. 2, ring segments 124 disposed adjacent the central portion 122 of the first tubular member 120 are connected by elongated struts 126. The elongated strut 126 provides greater flexibility between those adjacent ring segments 124 than between ring segments with standard (or non-elongated) struts. For example, the elongated struts 126 provided between ring segments 124 disposed adjacent the central portion 122 of the first tubular member 120 provide for greater flexibility between ring segments 124 than between those ring segment disposed adjacent the proximal end 123 or distal end 125 of the tubular member 120. As provided in FIG. 2, the central portion 122 of the first tubular member 120 includes at least four ring segments 124 coupled by elongated struts 126. The proximal and distal end 123, 125 portions disposed on opposing sides of the central portion 122 include at least two adjacent ring segments 124. However, in other implementations, the central portion 122 and proximal end 123 and distal end 125 include any number of ring segments 124. And, in other implementations, the adjacent ring segments 124 of the proximal and distal end 123, 125 portions are coupled by non-elongated struts/connectors 128.

Figure 3:
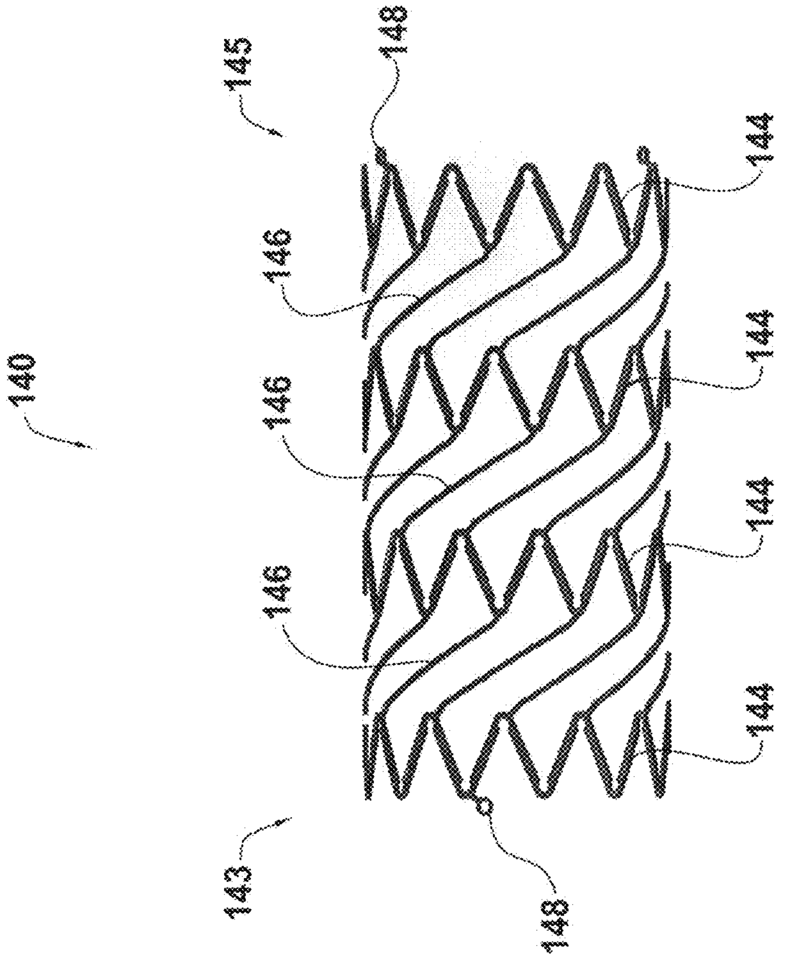
FIG. 3 is a side view of a second hollow tubular member of the stent in FIG. 1.

FIG. 3 provides a side view of an exemplary second hollow tubular member 140 according to one implementation. Similar to the first tubular member 120, the second tubular member 140 includes a plurality of ring segments 144 extending circumferentially around a perimeter of the second tubular member 140. At least some of the ring segments 144 are connected by an elongated strut 146. As illustrated in FIG. 3, each of the ring segments 146 of the second tubular member 140 are connected by elongated struts 146. Similar to elongated struts 126 described above, the elongated strut 146 provides greater flexibility between adjacent ring segments 144 than between those ring segments with standard (or non-elongated) struts. As shown, the second tubular member 140 includes at least two ring segments 144. However, in other implementations (not shown), the second tubular member 140 includes adjacent ring segments 144 coupled by non-elongated struts/connectors 148, similar to those ring segments located at the proximal and distal ends 123, 125 of the first tubular member 120. As illustrated in FIG. 3, the second tubular member 140 generally has a shorter length than the first tubular member 120. However, in other implementations, the second tubular member 140 is as long as, or longer than, the first tubular member 120.

As described above, elongated struts 126, 146 provide greater flexibility between adjacent ring segments than between those ring segments with standard (or non-elongated) struts. As provided in FIGS. 2 and 3, the elongated struts 126, 146 have a longitudinal length (L) greater than the longitudinal length (I) of an adjacent ring segment. In other implementations, the elongated struts 126, 146 have a longitudinal length (L) equal to or less than the longitudinal length (I) of an adjacent ring segment. As illustrated in FIGS. 2 and 3, the longitudinal length (L) of the elongated struts 126, 146 on the tubular member is consistent along the entire length of the tubular member. For example, in the implementation, the first tubular member 120 (or second tubular member 140) includes a first pair adjacent ring segments 124 separated by a first set of elongated struts 126*a*, a second pair of adjacent ring segments 124 connected by a second set of elongated struts 126*b*, and a third pair of adjacent ring segments 124 connected by a third set of elongated struts 126*c*. FIG. 2 illustrates that the longitudinal length of the first, second and third set of elongated struts 126*a*, 126*b*, 126*c* is the same. However, in other implementations, the longitudinal length of the elongated struts 126, 146 between various ring segments 124, 144 varies along the length of the tubular member.

In some implementations, the elongated struts 126, 146 of the first and second tubular members 120, 140 are made from the same material as the corresponding ring segments 124, 144. And, in other implementations, the elongated struts 126, 146 are made from a different material as the corresponding ring segments 124, 144. For example, the ring segments 124, 144 and the elongated struts 126, 146 of the corresponding tubular member include wires of different metals. In addition, in some implementations, the elongated struts 126, 146 also have a thickness different from the thickness of the lattice member/wire of the ring segments 124, 144 of the corresponding first and second tubular members 120, 140. For example, as illustrated in FIGS. 1-3, the elongated struts 126, 146 have a thickness less than the thickness of the lattice member/wire of the ring segments 124, 144 of the corresponding first and second tubular members 120, 140.

As illustrated in FIGS. 1-3, the ring segments 124, 144 extend circumferentially around the perimeter of each tubular member 120, 140. For example, in some implementations, the ring segments 124, 144 extend circumferentially around the tubular members in an undulating pattern. In another implementations, the ring segments 124, 144 extend around the tubular member in a zig-zag or sinusoidal pattern. As illustrated in FIGS. 2 and 3, the elongated struts 126, 146 extend around a portion of the circumference of the tubular member. For example, the individual elongated struts 126, 146 extend between offset and opposing apexes of the undulating pattern of adjacent ring segments.

As outlined above, the first tubular member 120 and the second tubular member 140 are coupled together such there is overlap of the two members. FIG. 1 illustrates the second tubular member 140 disposed over the first tubular member 120. However, in other implementations, the first tubular member 120 is disposed over the second tubular member 140. In the implementation shown in FIG. 1, the second tubular member 140 is coupled to the first tubular member 120 such that the central portion 122 of the first tubular member 120 is disposed adjacent the central portion 142 of the second tubular member 140. In another implementation (not shown), the second tubular member 140 is coupled to/extends over the first tubular member 120 at a proximal or distal end 123, 125 of the first tubular member 120. As provided in FIG. 1, the first and second tubular members 120, 140 are layered such that the elongated struts 126, 146 of the corresponding tubular members extend around the stent 100 in different directions. The layering of the first and second tubular members 120, 140 and the overlap of elongated strut sections 126, 146, increases the radial strength of the stent 100, which helps to keep calcified lesions open, allows the stent 100 to be flexible, which helps the stent 100 travel through and conform to tortuous vessels, and reduces the area between stents struts 126, 146/overlapping lattice structure to prevent plaque from embolizing through the stent 100.

According to some implementations, the first and second tubular members 120, 140 are slidably coupled together such that the first and second tubular members 120, 140 are moveable in both longitudinal and rotational directions with respect to the other. For example, the tubular members are connected at corresponding connectors 128, 148 disposed on the first and second tubular members 120, 140, respectively. As illustrated in FIGS. 2 and 3, the connectors 128, 148 extend axially from a ring segment 124, 144 of the first and second tubular members 120, 140. The connectors 128, 148 are disposed between opposing apexes of adjacent ring segments. In other implementations, each of the first and second tubular members 120, 140 include a plurality of connectors 128, 148. The connectors 128, 148 include an opening that receives a coupling member (not shown). The coupling member extends through a respective opening to fix the two connectors together. An exemplary coupling member includes a radio-opaque marker. In other implementations, the first and second tubular members 120, 140 are coupled to/fixed together to prevent relative movement between members 120, 140.

According to various implementations, the first and second tubular members 120, 140 include a wire, a sheet metal, or tube. The ring segments 124, 144 and elongated struts 126, 146 of the first and second tubular members 120, 140 define lattice structures/members. For example, the ring segments 124, 144 and/or elongated struts 126, 146 define an open structure, a closed structure, or braided lattice structure.

In addition, according to various implementations, the first and second tubular members 120, 140 are formed from a variety of biocompatible materials, such as cobalt chromium, titanium and titanium alloys, stainless steel, nitinol, platinum, gold, or other metals, as well as ceramics or polymers. In addition, the first and second tubular members 120, 140 include a coated or sheathed material. For example, the first and second tubular members 120, 140 include a bioresorbable material or have a bioresorbable coating or sheathing.

Figure 13A:
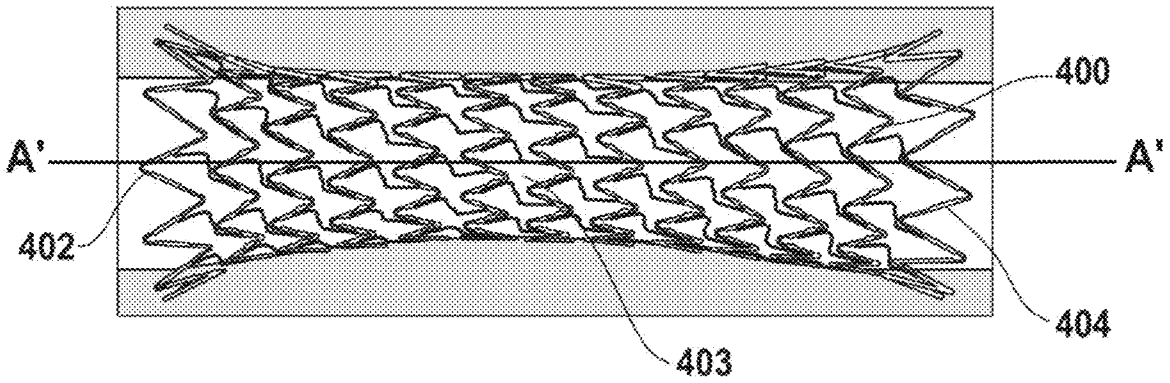

FIGS. 13A-13D illustrate a stent 400 according to another implementation. The stent 400 is a single layer stent that has an hourglass shape when deployed, as viewed from the side as shown in FIG. 13A. In particular, a diameter of the stent 400 varies along a longitudinal axis A'-A' extending through the stent 400. A mid portion 403 of the stent 400 has a diameter that corresponds to a diameter of the vessel in which the stent 400 is being deployed, and the diameter of the stent 400 increases parabolically along the longitudinal axis A'-A' from the mid portion 403 to each flared end 402, 404, forming the hourglass shape. In some implementations, the diameter at end 402 is the same as the diameter at end 404, and in other implementations, the diameter at one end 402, 404 is larger than the diameter at the other end 404, 402. In some implementations, the diameter at the mid portion 403 is half of the diameter at the flared ends 402, 404. The hourglass shape of the stent 400 and the flared ends 402, 404 allow for better apposition to the vessel wall, especially in tortuous vessel anatomy.

In addition, the stent 400 has a plurality of ring segments 403 having a sinusoidal pattern extending around the circumference of the stent 280. Elongated struts 407 having a z-shape extend between axially adjacent rings 403. The struts 407 are coupled to a portion of each ring 403 between adjacent apexes 405, 406. Each strut 407 has a bend at a central portion 408 thereof that extends circumferentially from the ends 409, 411 thereof. In the implementation shown in FIGS. 13A-13D, the stent 400 has thirteen rings and twelve rows of elongated struts coupling adjacent rings.

FIGS. 14A-14C illustrate a stent 500 according to another implementation. Like stent 400, stent 500 is also a single layer stent having an hourglass shaped when deployed, but the elongated struts 507 are arranged differently than with stent 400. In particular, the elongated struts 507 of stent 500 extend between axially adjacent apexes on a first ring to between adjacent apexes on a second, adjacent ring, but the central portion 508 of the strut 507 is disposed between a right facing apex 405 of one ring and a left facing apex 406 of an adjacent ring. The strut 507 forms an s-shape, and the struts 507 in each row have the same orientation.

FIGS. 15A-15C illustrate a stent 600 according to another implementation. Stent 600 is similar to stent 500 except that the elongated struts 607*a*, 607*b* between the rings have alternating orientations. In particular, the orientation of the struts 607*a* between a first ring and a second ring are in one direction, and the orientation of the struts 607*b* between the second ring and a third ring are in the opposite, or mirror image, direction.

FIGS. 4-9 provide various views of an exemplary percutaneous transluminal angioplasty device 200 according to one implementation. The stents 100, 400, 500, 600 described above in relation to FIGS. 1-3 and 13A-15C or any other suitable stent structure known in the art is usable with the angioplasty device 200. According to the implementation shown in FIGS. 4-9, the angioplasty device 200 includes a catheter 220 having one or more axial lumens extending at least partially through the catheter, an integrated filter assembly 240, an expandable balloon 260, a stent 280, and an axially movable sheath 284.

Figure 4:
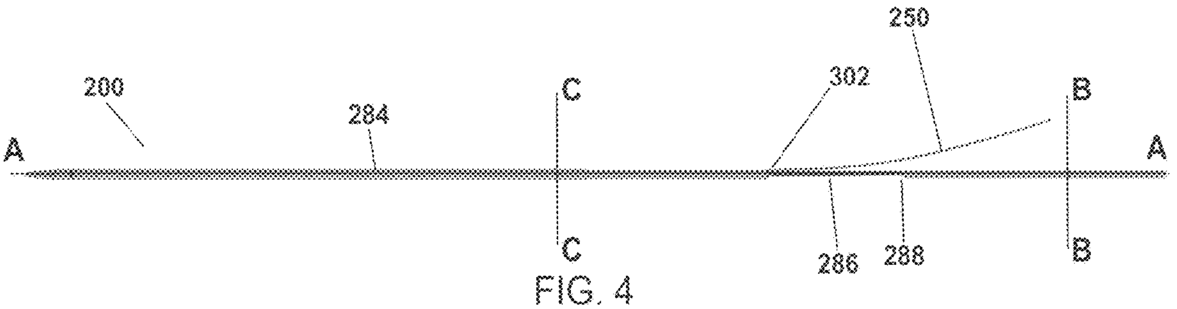
FIG. 4 is a side view of an exemplary percutaneous transluminal angioplasty device according to one implementation.

FIG. 4 is a side view of the percutaneous transluminal angioplasty device 200 with the sheath 284 covering the filter assembly 240, stent 280, and balloon 260. FIGS. 5-7F illustrate the configuration and operation of the device 200 as the filter assembly 240 and stent 280 are deployed and the filter assembly 240 is then collapsed and removed with the device 200, leaving the stent 280 in place within the body.

Figure 16:
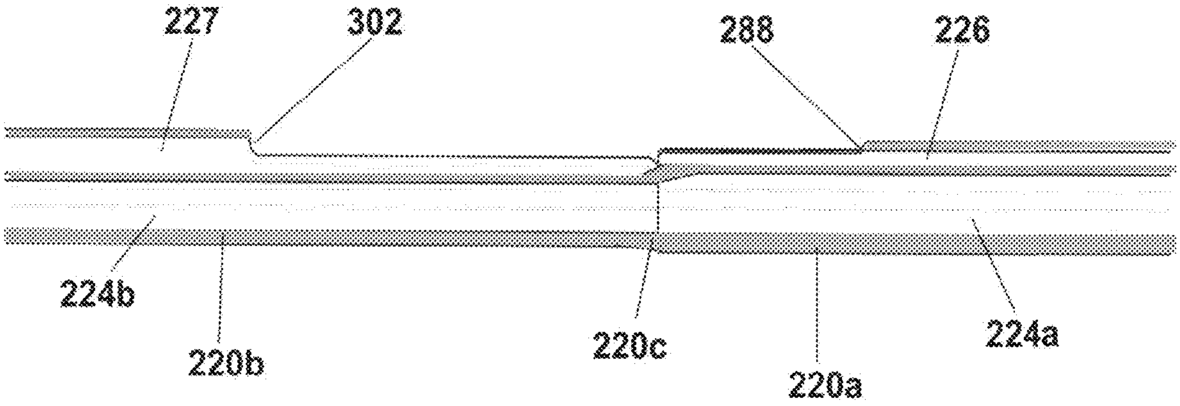
FIG. 16 illustrates a cross sectional view of the catheter shown in FIG. 4 as taken along the longitudinal axis A-A.

In the implementation shown in FIGS. 4 and 16, the device 200 includes a catheter 220 having a proximal end 225 and a distal end 223. The catheter 220 has a proximal portion 220*a* that is disposed adjacent the proximal end 225 and a distal portion 220*b* that is disposed adjacent the distal end 223. The proximal portion 220*a* and the distal portion 220*b* are coupled together at mid portion 220*c*. For example, the proximal portion 220*a* and the distal portion 220*b* are integrally formed together at mid portion 220*c* according to some implementations. And, in other implementations, the portions 220*a*, 220*b* are formed separately and coupled together at mid portion 220*c* using thermal or chemical bonding mechanisms, for example. In other implementations, the catheter 220 includes one or more portions, and the number of portions depends at least in part on the control components to be provided by the device.

Figure 8:
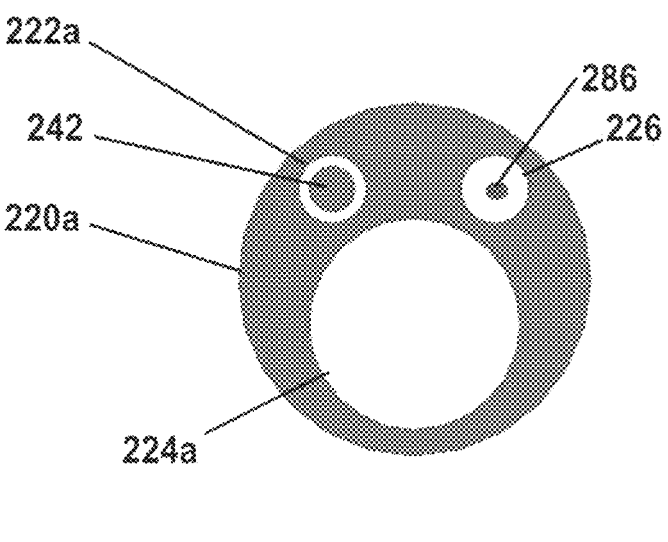
FIG. 8 is a cross sectional view of the percutaneous transluminal angioplasty device as taken through the B-B line of FIG. 4.
Figure 9:
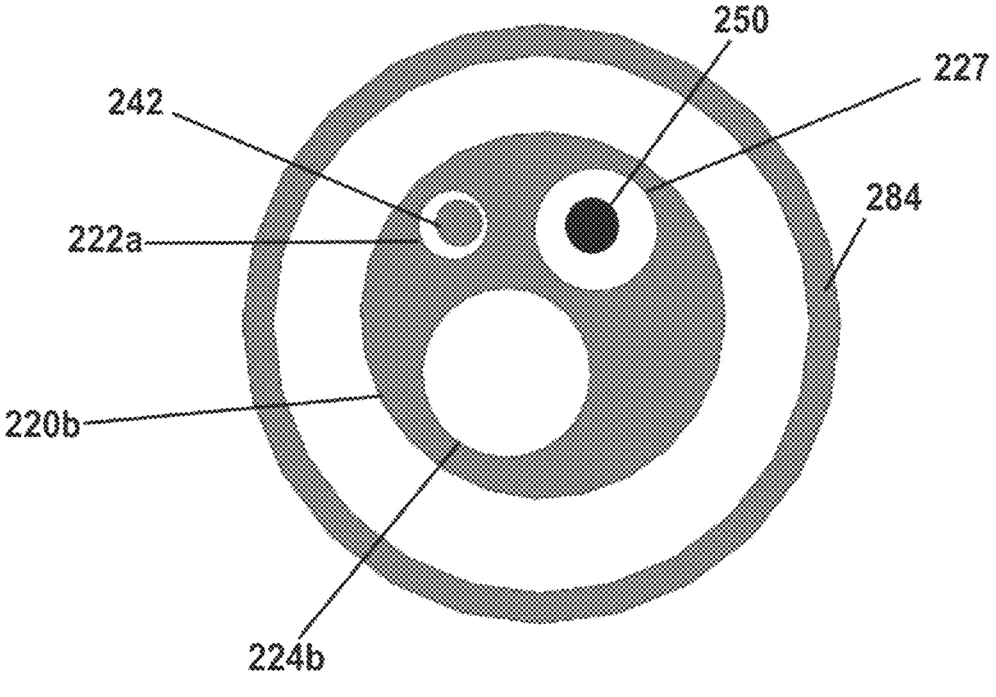
FIG. 9 is a cross sectional view of the percutaneous transluminal angioplasty device as taken through the C-C line of FIG. 4.

FIG. 8 illustrates a cross sectional view of the proximal portion 220*a* of the catheter 220 as taken through line B-B as shown in FIG. 4, and FIG. 9 illustrates a cross sectional view of the distal portion 220*b* of the catheter 220 as taken through line C-C as shown in FIG. 4, according to one implementation. The cross sectional views in FIGS. 8 and 9 illustrate an exemplary arrangement of one or more lumens extending through at least a portion of the catheter 220. As shown in FIG. 8, the proximal portion 220*a* defines a proximal balloon inflation lumen 224*a*, a sheath wire lumen 226, and a proximal filter activation wire lumen 222*a*. And, as shown in FIG. 9, the distal portion 220*b* defines a distal balloon inflation lumen 224*b*, a distal filter activation wire lumen 222*b*, and a guidewire lumen 227. In some implementations, the proximal and distal balloon inflation lumens 224*a*, 224*b* are axially aligned, and in other implementations, the lumens 224*a*, 224*b* are in communication with each other but are not axially aligned. Similarly, in some implementations, the proximal and distal filter activation wire lumens 222*a*, 222*b* are axially aligned, and in other implementations, the lumens 222*a*, 222*b* are in communication with each other but are not axially aligned. And, in some implementations, the sheath wire lumen 226 is axially aligned with the guidewire lumen 227, and other implementations, the sheath wire lumen 226 and the guidewire lumen 227 are not axially aligned. Further, in some implementations, the sheath wire lumen 226 and the guidewire lumen 227 are in communication with each other, regardless of their axial alignment. In addition, in some implementations, distal ends of one or more of lumens 222*a*, 224*a*, 226 in the proximal portion 220*a* of the catheter 220 are axially spaced apart from proximal ends of one or more lumens 222*b*, 224*b*, 227 in the distal portion 220*b* of the catheter 220. And, in some implementations, the distal ends of one or more lumens 222*a*, 224*a*, 226 abut the proximal ends of one or more lumens 222*b*, 224*b*, 227 in the distal portion 220*b* of the catheter 220.

According to various implementations, the lumens are sized to accommodate various control components passing through the lumens, and the orientation, sizes, and/or number of lumens shown in FIGS. 8 and 9 is selected depending on the components to be controlled by the device 200. In addition, the control components described above in relation to FIGS. 4-9 are exemplary, and, in other implementations, the device includes more or less control components and/or lumens, depending on the intended use of the device. Furthermore, the lumens described above in relation to FIGS. 4-9 receive one control component each, but in other implementations, one or more lumens are sized to receive one or more control components.

As illustrated in FIGS. 4-7F, the device 200 further includes a distal tip 235 coupled to the distal end 223. In the implementation shown in FIGS. 4-7F, the distal tip 235 is conical or frusto-conically shaped to facilitate penetration through the body. The tip 235 defines a guidewire port through which a guidewire 250 extends during placement of the device 200 within the body. The tip 235 according to one implementation includes a low durometer material, such as PEBAX. However, in other implementations, the tip includes other suitable shapes (e.g., spherical or hemispherical, pyramidal, blunted) depending on the intended path of the tip through the body.

Figure 5:
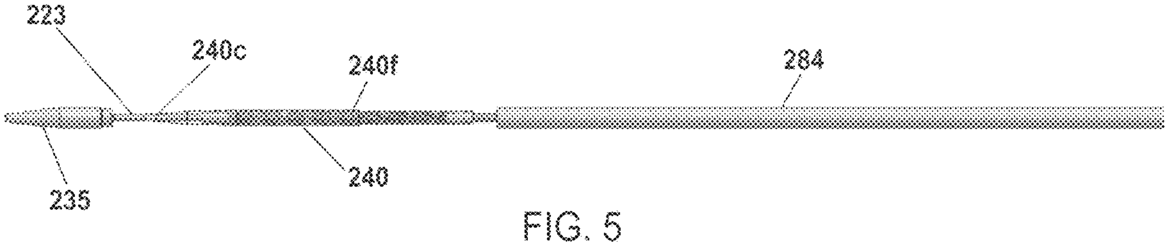
FIG. 5 is a side view of the percutaneous transluminal angioplasty device shown in FIG. 4 with the filter assembly exposed and unexpanded.

According to the implementation shown in FIGS. 4-7F, the filter assembly 240 is coupled to the distal portion 220*b* of the catheter 220 adjacent the distal end 223 of the catheter 220 and is disposed axially proximal to the tip 235. The filter assembly 240 is moveable between an expanded and unexpanded configuration. The filter assembly 240 in the unexpanded configuration, which is illustrated in FIGS. 5 and 7E, is sized and configured for insertion and passage through a blood vessel. In the expanded configuration, illustrated in FIGS. 6 and 7A-7D, the filter assembly 240 is sized and configured to capture emboli within the bloodstream. For example, at least a portion of the filter assembly 240 in the expanded configuration extends across a diameter of the vessel to catch emboli that may be flowing through the bloodstream.

The filter assembly 240 includes a filter membrane 240*a* and a filter frame 240*b*. The filter membrane 240*a* is frusto-conically shape, and the filter frame 240*b* is egg shaped in the implementations shown in FIGS. 5-7D. A conical tip 240*c* of the membrane 240*a* is fixedly coupled around the distal portion 220*b* of the catheter 220, and a distal end 240*e* of the filter frame 240*b* is disposed proximally of the conical tip 240*c* of the membrane 240*a* and is slidably coupled around the distal portion 220*b*. A proximal portion 240*f* of the filter membrane 240*a* is fixedly coupled to a central portion 240*g* of the filter frame 240*b*, such as via thermal or chemical bonding or another suitable coupling mechanism. And, a proximal portion 240*d* of the filter frame 240*b* is fixedly coupled around the distal portion 220*b*. In other implementations, the shape of the membrane and/or filter frame may be different than shown in FIGS. 5-7D and may be based at least in part on the anatomy in which the filter assembly is to be disposed.

Figure 6:
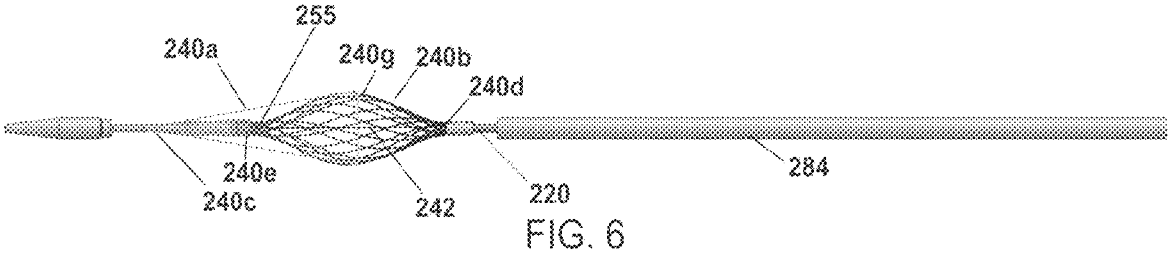
FIG. 6 is a side view of the percutaneous transluminal angioplasty device shown in FIG. 4 with the filter assembly expanded.
Figure 7A:
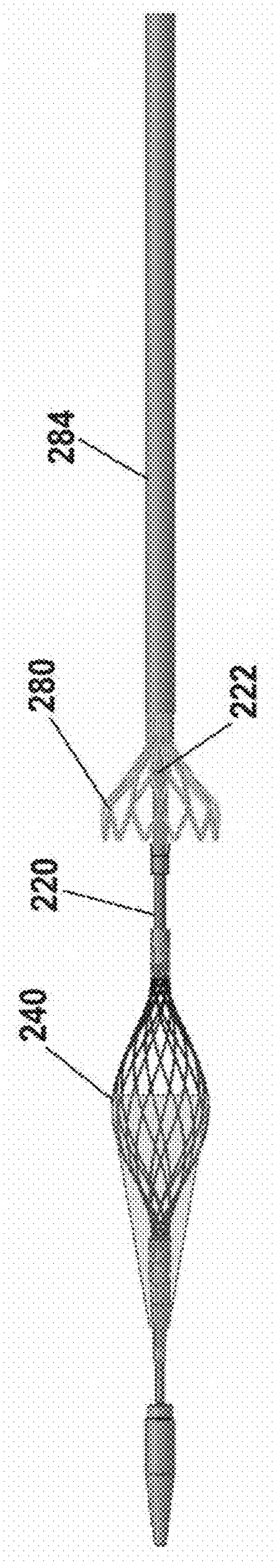
FIGS. 7A-7F is a side view of the percutaneous transluminal angioplasty device of FIG. 4 with the movable sheath retracted in various positions to show the expansion of a stent and inflation of the balloon and the operation of the device to set the stent in the body.
Figure 7B:
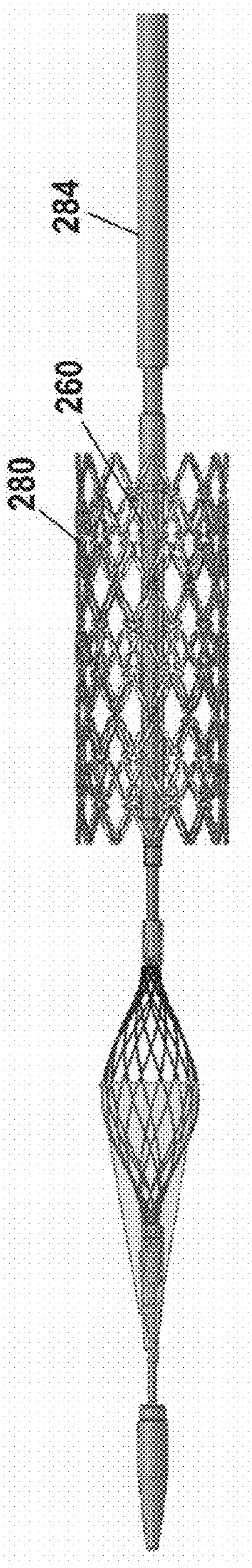
Figure 7C:
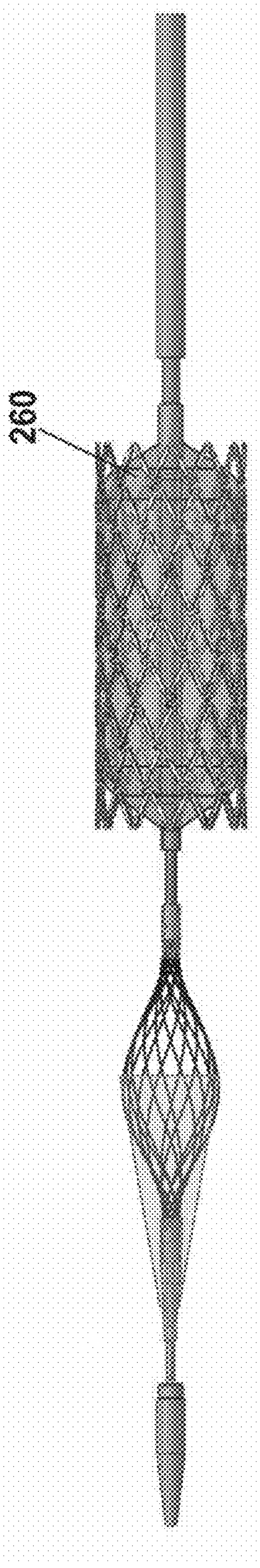
Figure 7D:
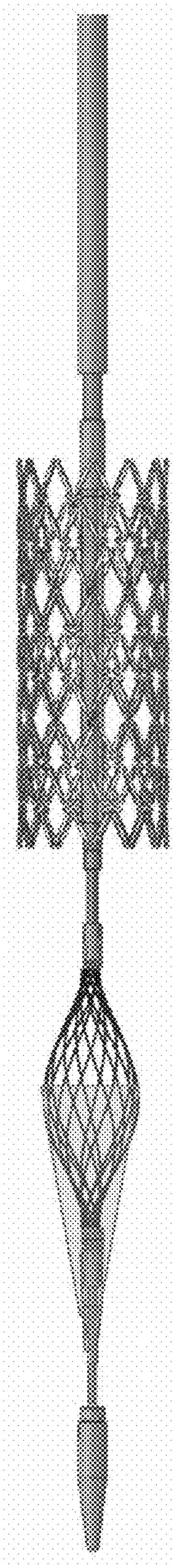
Figure 7E:
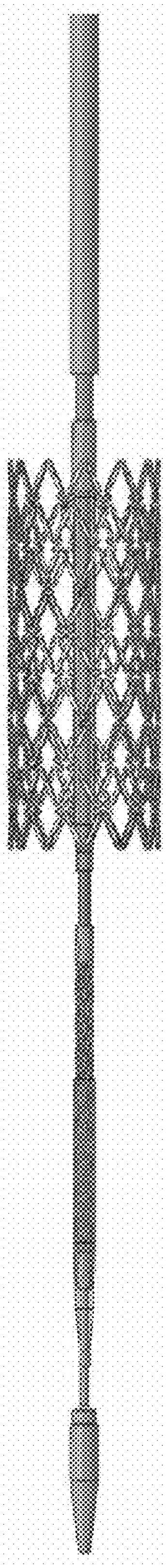
Figure 7F:
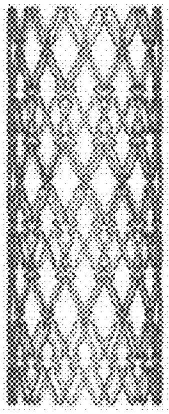

Referring now to FIGS. 6, 8, and 9, a filter activation wire 242 extends through the filter activation wire lumens 222*a*, 222*b*, and a distal end of the filter activation wire 242 extends through a filter activation wire port 255 and is coupled to the distal end 240*e* of the filter frame 240*b*. The filter activation wire port 255 is defined by the distal portion 220*b* of the catheter 220. The filter activation wire port 255 has a first opening and a second opening. The first opening is defined by an external surface of the distal portion 220*b* of the catheter 220 and is disposed between the distal end 240*e* of the filter frame 240*b* and the proximal end 240*d* of the filter frame 240*b*. The second opening is defined by lumen 222*b*. In some implementations, the second opening of the port 255 is axially proximal the first opening, and in other implementations, the first and second openings of port 255 are radially aligned. The filter activation wire port 255 is distally disposed relative to the expandable balloon 260 and stent 280.

Tensioning the filter activation wire 242 in the proximal direction causes the distal end 240*e* of the filter frame 240*b* to move proximally, which causes the filter assembly 240 to move from the unexpanded configuration to the expanded configuration. Similarly, releasing tension on the filter activation wire 242 allows the filter assembly 240 to move into the unexpanded configuration. In the expanded position, an outer diameter of the filter frame 240*b* around the central portion 240g and an outer diameter of the proximal portion 240*f* of the filter membrane 240*a* correspond to an inner diameter of an artery or vessel to ensure that any embolic material is captured by the filter assembly 240. In addition, the filter membrane 240*a* and the filter frame 240*b* allow blood/fluid to flow therethrough.

According to some implementations, the filter membrane 240*a* comprises a biocompatible, elastic polymer sheet (e.g., polyurethane) that defines an array of openings. In certain implementations, the openings are 40 micrometers in diameter, which allows blood to flow through but captures small particulates. And, in some implementations, the openings are formed by laser drilling. In addition, in various implementations, the filter frame 240*b* comprises a biocompatible, expandable structure that defines a plurality of openings. The openings of the filter frame 240*b* are larger than the openings defined by the filter membrane 240*a*. The filter frame 240*b*, according to some implementations, includes a material having memory properties, such as a braided nitinol structure or a laser cut nitinol tube structure. Other suitable biocompatible materials include titanium and titanium alloys, stainless steel, platinum, gold, or other metals, as well as ceramics or polymers. In some implementations, the filter frame 240*b* has a memory of the unexpanded configuration such that when tension on the filter activation wire 242 is released, the filter frame 240 returns toward its unexpanded configuration, capturing any embolic materials that have been captured within the filter assembly 240.

In the implementation shown in FIGS. 4-7F, the expandable balloon 260 is disposed between the proximal end 240*d* of the filter frame 240*b* and the proximal end of the distal portion 220*b* of the catheter 220. Air and/or fluid is provided to the balloon 260 for inflation via the balloon inflation lumens 224*a*, 224*b* defined by the proximal portion 220*a* and distal portion 220*b* of the catheter 220, as shown in FIGS. 8, 9, and 16. In some implementations, a tube, such as a hypotube, is disposed within the balloon inflation lumens 224*a*, 224*b* for delivering the air/fluid to the balloon 260. A distal balloon inflation port (not shown) is defined by the distal portion 220*b* of the catheter 220 and extends between the balloon inflation lumen 224*b* and a portion of the external surface of the distal portion 220*b* that is in fluid communication with an inside of the balloon 260.

The stent 280 is disposed over at least a portion of the balloon 260. According to some implementations, the stent 280 is a self-expanding stent constrained in place over at least a portion of the balloon 260. For example, the stent 280 includes a stent similar to any of the self-expanding stents 100, 400, 500, 600 described above in relation to FIGS. 1-3 and 13A-15C. In other implementations, the stent 280 is a controlled/directed expansion stent. For example, in such implementations having a controlled/directed expansion stent, a stent deployment wire is coupled to the stent to direct expansion and contraction of the stent. A stent deployment wire lumen may also be defined in at least the proximal portion 220*a* through which the stent deployment wire is disposed. In other implementations, the stent is a balloon-expandable stent. The selection of the type, dimensions, and/or radial strength of the stent is based at least in part on the anatomy in which the stent is being deployed.

In the implementation illustrated in FIGS. 4-7F, the stent 280 is constrained by a movable sheath 284 or another type of restraining element. Exemplary sheaths include a wire, coiled wire, polymer filament, or polymer braid sheath. For example, in some implementations, the sheath 284 comprises an inner polymer layer (e.g., PTFE composite) to reduce friction with components disposed radially within the sheath 284, a structural sheath layer (e.g., a wire, coiled wire, polymer filament, or polymer braid sheath layer (e.g., a braided stainless steel sheath layer)) to maintain the radial strength of the sheath 284, and an outer polymer layer (e.g., nylon) to protect the structural sheath layer. In addition, the sheath 284 is a 6F sheath/8F guide compatible sheath, according to one implementation. The movable sheath 284 extends over the stent 280 and filter assembly 240 in the implementation shown in FIG. 4. However, in some implementations, the sheath 284 does not extend over the filter assembly 240, and in other implementations, the sheath 284 extends over a portion of the filter assembly 240.

Figure 12:
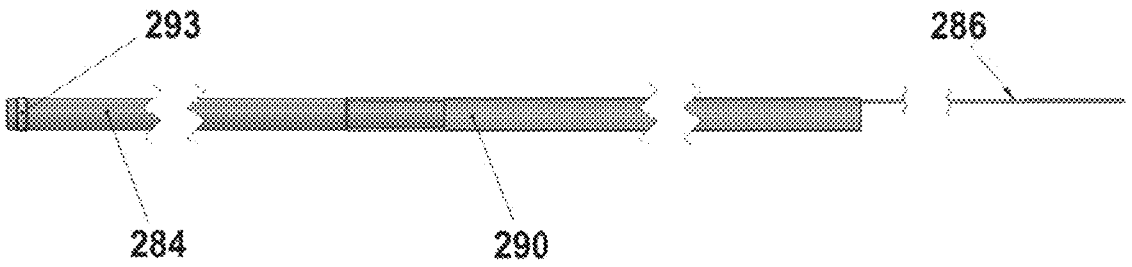
FIG. 12 illustrates a side view of portions of the sheath according to one implementation.

Furthermore, in the implementation shown in FIG. 12, the sheath 284 includes a radio-opaque marker 293 around a portion of the sheath 284 to assist in locating the stent 280 within the body prior to stent deployment. However, in other implementations, the sheath 284 may not include the radio-opaque marker 293. In addition, in some implementations, the sheath 284 may be tapered from its distal end toward its proximal end, wherein the distal end of the sheath 284 has a larger diameter than the proximal end of the sheath 284.

As shown in FIG. 16, a sheath wire exit port 288 is defined between an external surface of the proximal portion 220*a* of the catheter 220 and the sheath wire lumen 226, and a sheath wire 286 extends between the sheath wire lumen 226 and the sheath 284 via the sheath wire exit port 288. In one implementation, the sheath wire exit port 288 is defined adjacent a distal end of the proximal portion 220*a* of the catheter 220. A distal end of the sheath wire 286 is coupled to the sheath 284. In some implementations, the sheath wire 286 is coupled to the sheath 284 by embedding the distal end of the sheath wire 286 between the braided structural layer and the outer polymer layer.

By disposing the sheath wire 286 within the proximal portion 220*a* of the catheter 220, the physician is able to stabilize (e.g., hold steady) the catheter 220 while the sheath 284 is moved axially proximal to the stent 280, which reduces or prevents movement of the distal portion 220*b* of the catheter 220 and unintentional axial movement of the stent relative to the target location during deployment of the stent (also known as "stent jumping"). In known devices, the sheath is not coupled to a sheath wire, and the sheath extends proximally over the entire length of the catheter. Thus, there is no space available on the catheter to hold the catheter steady during sheath deployment. Known devices do not include a sheath wire.

Figure 17A:
FIG. 17A illustrates a side view of the catheter in FIG. 4 having a sleeve, according to one implementation.
Figure 17B:
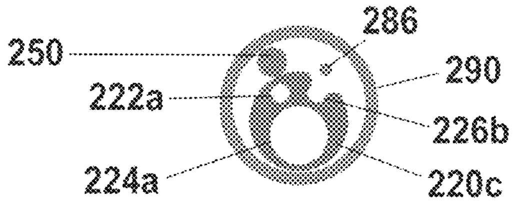
FIG. 17B illustrates a cross sectional view of the catheter and sleeve in FIG. 17A as taken through the D-D line.

In the implementation shown in FIG. 4, a portion of the sheath wire 286 extending between the sheath wire lumen 226 and the sheath 284 is exposed. However, in some implementations, such as is shown in FIGS. 12 and 17A and 17B, a sleeve 290 (e.g., a polymer sleeve) is disposed at least partially around the exposed portion of the sheath wire 284 and the mid portion 220*c* of the catheter. At least a portion of the exterior surface of mid portion 220*c* defines a recessed, axially extending groove 226*b* that is in communication with the sheath wire lumen 226 defined by the proximal portion 220*a*. The sheath wire 286 is radially movable in and out of the groove 226*b*. In the implementation shown, guidewire 250 is routed through a proximal end of the sleeve 290 toward the guidewire lumen 227 defined by the distal portion 220*b* of the catheter 220. In the implementation shown in FIGS. 12 and 17A, the sheath 284 and the sleeve 290 are coupled together. However, in other implementations, the sheath 284 and sleeve 290 are separately formed and disposed axially adjacent each other.

In the implementation shown in FIGS. 4 and 16, a proximal end of the distal portion 220*b* of the catheter 220 defines a guidewire port 302 that extends between the guidewire lumen 227 and an external surface of the catheter 220. The opening of the guidewire port 302 defined by the external surface of the catheter 220 is proximal to guidewire lumen 227 to facilitate rapid exchange of the guidewire 250. In the implementation shown, the guidewire port 302 is defined by the opening of the guidewire lumen 227 at the proximal end of the distal portion 220*b*. A proximal portion of the guidewire 250 extends out of the distal portion 220*b* of catheter 220 proximally of the sheath 284 via the guidewire port 302. The guidewire 250 according to some implementations has a diameter of between 0.010 inches and 0.038 inches (e.g., 0.014 inches). In other implementations, the guidewire port includes a first opening and a second opening. The first opening of the guidewire port is defined by the exterior surface of the catheter that is radially spaced apart from the guidewire lumen 227, and the second opening of the guidewire port is defined by an interior surface of the lumen 226 and is distally spaced apart from the first opening along the longitudinal axis of the guidewire lumen 227. That is, in various implementations, the guidewire port extends through the catheter 220 from a first opening towards a second opening defined by a lumen that is distally spaced from the first opening.

Figure 11:
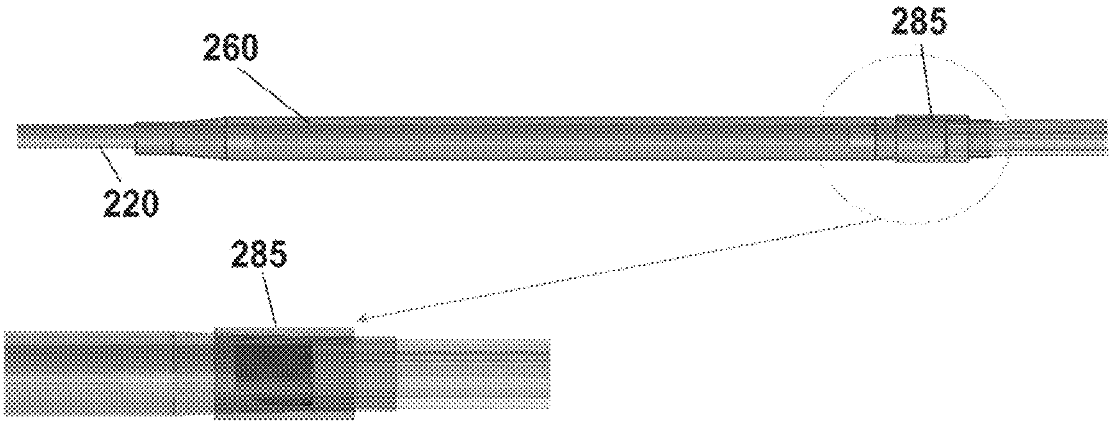
FIG. 11 illustrates a side view of a stent stop disposed on the catheter according to one implementation.

As illustrated in FIG. 11, a deployment stopper 285 is disposed proximally of the stent 280 (e.g., adjacent the proximal end of the balloon 260) to prevent the stent 280 from moving axially during removal of the sheath 284. In some implementations, the stopper 285 is a nylon stop that is adhesively bonded to the distal portion 220*b* of the catheter 220. The stopper 285 ensures that the working length of the balloon 260 is disposed within the length of the stent 280. And, the positioning of the stent 280 relative to the balloon 260 accounts for shortening of the stent 280 post deployment. In other implementations, the deployment stopper 285 is formed of any suitable material and is moveably or fixedly coupled to, integrally formed with, or independent of the movable sheath 284 and/or the distal portion 220*b* of the catheter 220.

The control component-lumen designations described herein are only exemplary implementations of the disclosed device and are in no way limiting as the only or preferred implementations. In another implementation (not shown), the catheter includes a fourth lumen that extends axially through at least a portion of the catheter. For example, in an implementation in which the sheath is removed by a sheath wire and the stent is expandable by moving a stent deployment wire, the sheath deployment wire extends through the fourth lumen. However, in some implementations, the stent deployment wire is disposed within the lumen of the sheath wire.

Figure 10A:
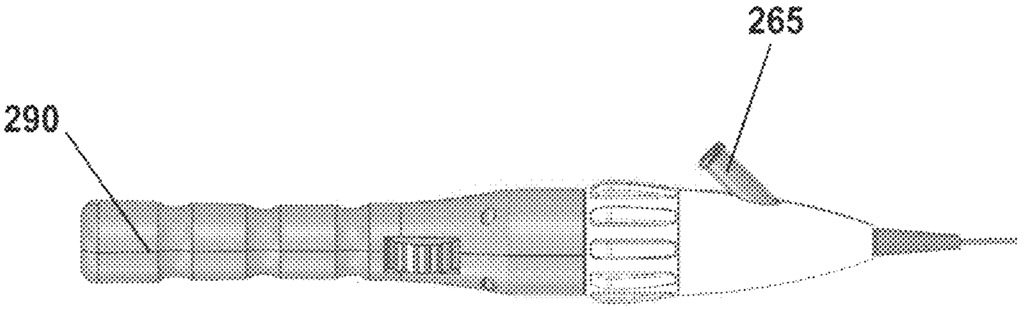
FIGS. 10A-10C illustrate a side view, partial cross sectional view, and an exploded view, respectively, of a handle according to one implementation.
Figure 10B:
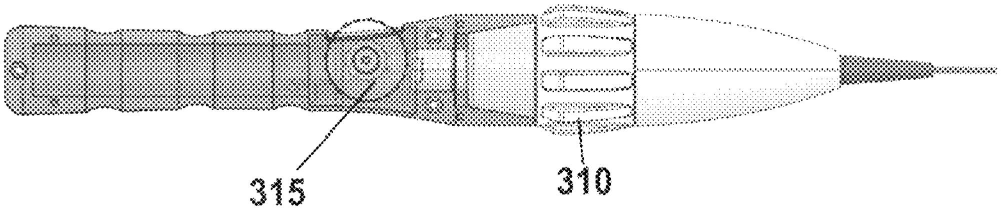
Figure 10C:
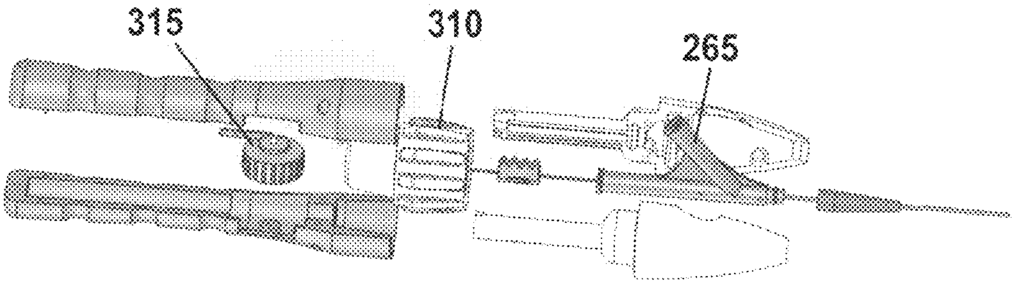

As shown in FIGS. 10A-10C, the device 200 further includes a handle 290 coupled to a proximal end 225 of the proximal portion 220*a* of the catheter 220. In some implementations, the handle 290 includes controls (e.g., buttons, knobs, etc.) that are coupled to one or more of the filter activation wire 242, the sheath wire 286, and/or the guidewire 250 to allow the user to actuate the filter 240, the sheath 284, and/or the guide wire 250. In the implementation shown in FIGS. 10A-10C, knobs 310, 315 are disposed on the handle 290 and are coupled to the filter activation wire 242 and the sheath wire 286, respectively. Actuation of the knobs 310, 315 in one direction causes the respective wires to be tensioned proximally, and actuation of the knobs 310, 315 in the opposite direction releases tension on the wires. In addition, as shown in FIG. 10A, the handle 290 defines a proximal balloon inflation port 265 that is in fluid communication with the balloon inflation lumens 224*a*, 224*b* and the balloon 260 to provide air/fluid to the balloon 260 for expansion.

As will be readily appreciated by those of skill in the art, various implementations of the percutaneous transluminal angioplasty device 200 and its corresponding components are formed from one or more biocompatible materials, such as cobalt chromium, titanium and titanium alloys, stainless steel, nitinol, platinum, gold, or other metals, as well as ceramics or polymers. In addition, in some implementations, the device 200 or portions thereof includes a coated or sheathed material. For example, the device 200 includes a bioresorbable material or has a bioresorbable coating or sheathing.

In use, the catheter 220 is advanced over guidewire 250 (e.g., under fluoroscopic guidance) to a target location/stenosis site within a blood vessel. FIGS. 7A-7F illustrate how the device 200 is operated within the body according to one implementation. First, the sheath 284 is moved axially toward the proximal end 225 of the device 200 to expose the filter assembly 240 by pulling the sheath wire 286 proximally to expose the filter assembly 240. Then, the filter assembly 240 is deployed into the expanded configuration by tensioning the filter activation wire 242. Deploying the filter assembly 240 prior to deploying the stent 280 allows the filter assembly 240 to catch any embolic material that is dislodged during deployment of the stent 280. Next, the sheath 284 is moved further axially toward the proximal end 225 to expose the stent 280. With the sheath 284 disposed proximally of the stent 280, the stent 280 expands radially based on the memory properties of the material of the stent 280 for implementations that include a self-expanding stent. In other implementations, other types of stents may be deployed once the sheath 284 is moved to expose the stent 280. Next, the balloon 260 is inflated against an inner surface of the stent 280 such that the stent 280 is further radially expanded against the vessel wall (post-dilatation expansion). This step of post-dilatation may be repeated to expand the stenosed region of the artery and expand the stent 280 further radially against/toward the vessel wall. For example, the post-dilatation step may be repeated until the vessel is fully dilated. For example, the balloon 260 is inflated (or deflated) via fluid/air provided to (or removed from) a central chamber of the balloon 260 via port 265. After the vessel is fully dilated, the balloon 260 is deflated, tension in the filter activation wire 242 is released, and the filter membrane 240*a* and the filter net 240*b* are collapsed by releasing the filter activation wire 242, which securely capture any embolic material captured by the filter assembly 240. The blocked vessel is opened and blood flow is restored. The filter assembly 240 is then contracted by actuating the filter activation wire 242, and the device 200, which includes the deflated balloon 260 and the contracted filter assembly 240, are removed from the vessel. The catheter 220 is moved axially out of the body, which pulls the filter assembly 240 holding any captured embolic material and the unexpanded balloon 260 axially through the stent 280 and out of the body. Because the filter assembly 240 is able to capture and hold the embolic material upon release of the filter activation wire 242, it is not necessary to move the sheath 284 distally over the filter assembly 240 prior to removal of the device 200 from the body, which reduces the time required for the procedure.

As noted above, when the sheath wire 286 is tensioned to pull the sheath 284 away from the stent 280, the proximal portion 220*a* and the distal portion 220*b* of the catheter 220 on which the stent 280 and balloon 260 are able to be steadied by the physician (e.g., by holding the proximal portion 220*a* of the catheter) to prevent or reduce movement of the proximal portion 220*a* and the distal portion 220*b* relative to the sheath 284.

Having one device 200 that allows the user to actuate a filter, an expandable balloon, and a sheath and/or stent activation wire reduces the time required to perform a vascular expansion procedure and reduces the potential for complications resulting from the procedure.

In some implementations, self-expanding stents 280 provide sufficient flexibility to move through tortuous vessels. The inventors have discovered that dilating a self-expanding stent 280 radially outwardly after the self-expansion of the stent 280 by expanding the balloon 260 against the inner surface of the stent 280 increases the diameter of the stent 280. Thus, post-dilatating a self-expanding stent with an expandable balloon after stent deployment is useful for treating vascular stenosis in the carotid artery and other tortuous vessels.

In other implementations, the stent is a controlled/directed expansion stent, and a stent deployment wire is actuated to deploy the controlled/directed expansion stent. And, in other implementations in which the stent is a balloon deployable stent, the stent is deployed by inflating the balloon 260 via the fluid/air provided to the central chamber of the balloon 260.

In addition, the various embodiments disclosed herein are adaptable for use in virtually any vessel where the capture emboli within the bloodstream is required for a therapeutic or diagnostic purpose. In addition, it is also anticipated that certain embodiments could be used for purposes other than medical, such as construction, manufacturing, and excavation, among others; accordingly, nothing herein is intended to limit application of the various embodiments to purely medical uses.

Accordingly, the subject matter described above is provided by way of illustration only and should not be construed as limiting. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. A percutaneous transluminal angioplasty device, comprising:

a multi-lumen catheter having a proximal portion and a distal portion, the multi-lumen catheter defining a first lumen, a second lumen, and a third lumen each extending through at least a portion of the multi-lumen catheter;

a filter disposed on the multi-lumen catheter and being movable between an unexpanded configuration and an expanded configuration;

a filter activation wire coupled to the filter and extending through at least a portion of the first lumen;

an expandable balloon disposed on the multi-lumen catheter;

a self-expanding stent extending over at least a portion of the expandable balloon;

a movable sheath extending over at least a portion of the self-expanding stent;

a sheath wire coupled to the movable sheath and extending through at least a portion of the second lumen;

a guidewire extending through at least a portion of the third lumen;

a first handle control coupled to the filter via the filter activation wire and configured to move the filter between the unexpanded configuration and the expanded configuration; and a second handle control independently operable from the first handle control, the second handle control coupled to the movable sheath via the sheath wire and configured to retract the movable sheath axially.

2. The percutaneous transluminal angioplasty device of claim 1, wherein the filter comprises:

a filter frame coupled to the filter activation wire, and a filter membrane including a membrane distal end fixedly coupled to the multi-lumen catheter, and a membrane proximal end fixedly coupled to the filter frame.

3. The percutaneous transluminal angioplasty device of claim 2, wherein the filter activation wire is coupled to a filter frame distal end, and wherein the first handle control tensions the filter activation wire and urges the filter frame distal end axially in a proximal direction to move the filter from the unexpanded configuration to the expanded configuration.

4. The percutaneous transluminal angioplasty device of claim 1, wherein the filter defines a radius in the expanded configuration that corresponds to an inner diameter of a blood vessel into which the filter is disposed.

5. The percutaneous transluminal angioplasty device of claim 1, wherein the multi-lumen catheter further comprises a balloon inflation lumen in fluid communication with the expandable balloon.

6. The percutaneous transluminal angioplasty device of claim 5, wherein the multi-lumen catheter further includes an inflation port in fluid communication with the balloon inflation lumen.

7. The percutaneous transluminal angioplasty device of claim 1, wherein the multi-lumen catheter defines a guidewire port defined by the third lumen.

8. The percutaneous transluminal angioplasty device of claim 1, wherein the first lumen is a filter activation wire lumen, wherein the proximal portion of the multi-lumen catheter comprises a proximal filter activation wire lumen and the distal portion of the multi-lumen catheter comprises a distal filter activation wire lumen, and wherein the proximal filter activation wire lumen and the distal filter activation wire lumen are axially aligned.

9. The percutaneous transluminal angioplasty device of claim 1, wherein the second lumen is a sheath wire lumen positioned in the proximal portion of the multi lumen catheter, wherein the third lumen is a guidewire lumen positioned in the distal portion of the multi-lumen catheter, and wherein the sheath wire lumen and the guidewire lumen are axially aligned.

10. The percutaneous transluminal angioplasty device of claim 9, wherein a distal end of the sheath wire lumen is positioned adjacent a proximal end of the guidewire lumen.

11. The percutaneous transluminal angioplasty device of claim 1 wherein rotation of the first handle control in a first direction applies tension to the filter activation wire in a proximal direction, and wherein rotation of the first handle control in a second direction opposite the first direction relaxes tension in the filter activation wire.

12. The percutaneous transluminal angioplasty device of claim 1, wherein rotation of the second handle control in a first direction applies tension to the sheath wire in a proximal direction, and wherein rotation of the second handle control in a second direction opposite the first direction relaxes tension in the sheath wire.

13. The percutaneous transluminal angioplasty device of claim 1, wherein the first handle control and the second handle control are coupled to a handle.

14. The percutaneous transluminal angioplasty device of claim 1, wherein the distal portion of the multi-lumen catheter and the proximal portion of the multi-lumen catheter are coupled together using thermal or chemical bonding.

15. The percutaneous transluminal angioplasty device of claim 1, wherein the distal portion of the multi-lumen catheter and the proximal portion of the multi-lumen catheter meet at a mid portion of the multi-lumen catheter, the percutaneous transluminal angioplasty device further comprising a sleeve covering the mid portion of the multi-lumen catheter.

16. A percutaneous transluminal angioplasty device, comprising:

a handle including a first handle control knob and a second handle control knob;

a catheter extending from the handle and including:

a proximal catheter portion coupled to the handle and including a sheath activation lumen, a proximal filter activation lumen, and a proximal balloon inflation lumen; and a distal catheter portion coupled to the proximal catheter portion at a mid portion, the distal catheter portion and including a guidewire lumen, a distal filter activation lumen in fluid communication with the proximal filter activation lumen, and a distal balloon inflation lumen in fluid communication with the proximal balloon inflation lumen;

a filter coupled to the distal catheter portion, the filter actuated between an unexpanded configuration and an expanded configuration by the first handle control knob via the proximal filter activation lumen and the distal filter activation lumen;

an expandable balloon coupled to the distal catheter portion proximally of the filter, the expandable balloon fluidly coupled to the distal balloon inflation lumen; and a sheath movable between an extended sheath position covering the expandable balloon and a retracted sheath position exposing the expandable balloon, wherein the sheath is actuated between the extended sheath position and the retracted sheath position by the second handle control knob via the sheath activation lumen.

17. The percutaneous transluminal angioplasty device of claim 16, wherein the distal filter activation lumen is axially aligned with the proximal filter activation lumen, and the distal balloon inflation lumen is axially aligned with the proximal balloon inflation lumen.

18. The percutaneous transluminal angioplasty device of claim 16, further comprising a filter activation wire extending between the filter and the first handle control knob through the proximal filter activation lumen and the distal filter activation lumen.

19. The percutaneous transluminal angioplasty device of claim 16, further comprising a sheath wire extending between the sheath and the second handle control knob through the sheath activation lumen.

20. The percutaneous transluminal angioplasty device of claim 16, further comprising a self-expanding stent extending over at least a portion of the expandable balloon.

* * * * *